United States Patent [19]

Newgard et al.

[11] Patent Number: 4,874,377

[45] Date of Patent: Oct. 17, 1989

[54] SELF-OCCLUDING INTRAVASCULAR CANNULA ASSEMBLY

[75] Inventors: Kent W. Newgard, Orange; Mark G. Gordon, Tustin, both of Calif.

[73] Assignee: Davis Newgard Revocable Family Living Trust, Calif. ; a part interest

[21] Appl. No.: 199,118

[22] Filed: May 26, 1988

[51] Int. Cl.$^4$ .......................... P61M 5/00; P61M 25/00
[52] U.S. Cl. ..................................... 604/167; 604/256; 251/149.1
[58] Field of Search ...................... 128/764; 251/149.1; 604/164–169, 256, 249

[56] References Cited

U.S. PATENT DOCUMENTS

| | | | |
|---|---|---|---|
| 2,682,874 | 7/1954 | Hickey | 128/214 |
| 2,707,953 | 5/1955 | Ryan | 128/214 |
| 3,620,500 | 11/1971 | Santomieri | 604/280 |
| 3,834,380 | 9/1974 | Boyd | 128/133 |
| 3,856,010 | 12/1974 | Moorehead et al. | 128/214.4 |
| 3,856,020 | 12/1974 | Kovac | 128/347 |
| 3,875,938 | 4/1975 | Mellor | 128/214.4 |
| 4,006,744 | 2/1977 | Steer | 128/214 R |
| 4,143,853 | 3/1979 | Abramson | 251/149.1 |
| 4,177,809 | 12/1979 | Moorehead | 128/214.4 |
| 4,192,304 | 3/1980 | Millet | 128/214.4 |
| 4,387,879 | 6/1983 | Tsuschinski | 604/149.1 |
| 4,392,856 | 7/1983 | Lichtenstein | 604/177 |
| 4,445,893 | 3/1984 | Bodicky | 604/165 |
| 4,512,766 | 4/1985 | Vailancourt | 604/169 |
| 4,683,916 | 8/1987 | Raines | 251/149.1 X |

OTHER PUBLICATIONS

Brochure–"Percutaneous Valvuloplasty Catheter Accessories" 1987, by Cook Incorporated.

Primary Examiner—Dalton L. Truluck
Attorney, Agent, or Firm—Stetina and Brunda

[57] ABSTRACT

Disclosed is a self-occluding cannula assembly comprising a cannula sheath having a connector hub formed on one end thereof. A self-actuating occluding means is formed within the cannula assembly so as to prevent back flow of body fluids from the cannula. In the cannulae wherein an introducer needle is initially axially positioned within the cannula lumen, the occluding means will permit desired withdrawal of the needle but will thereafter immediately occlude the cannula lumen to prevent back flow therethrough. The occluding means is further adapted to shift to a "non-occluded" configuration upon connection of a second infusion or monitoring tube to the proximal end of the cannula. If, during use, the infusion/monitoring tube should become disconnected, the occluding means will again shift to its "occluded" configuration so as to prevent back flow of fluids from the cannula until such time as the infusion/-monitoring line is reconnected.

8 Claims, 1 Drawing Sheet

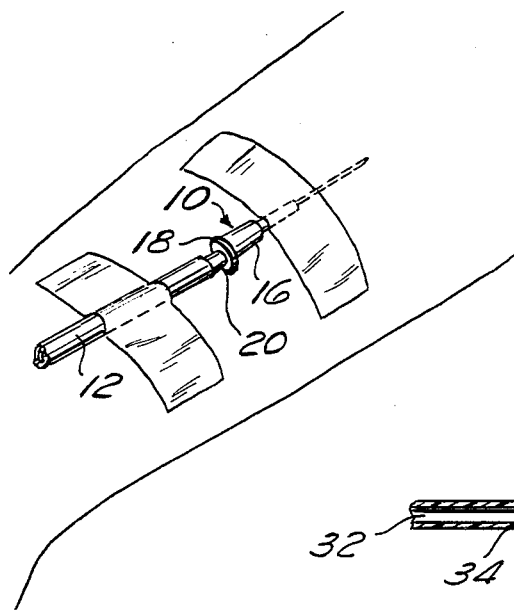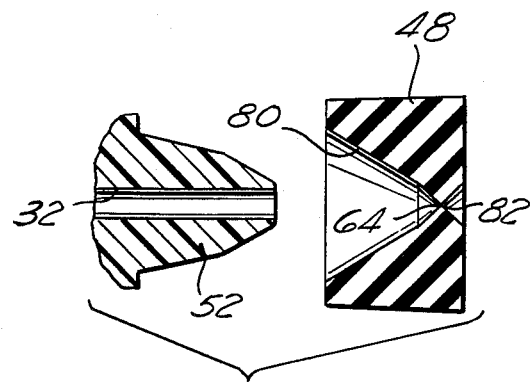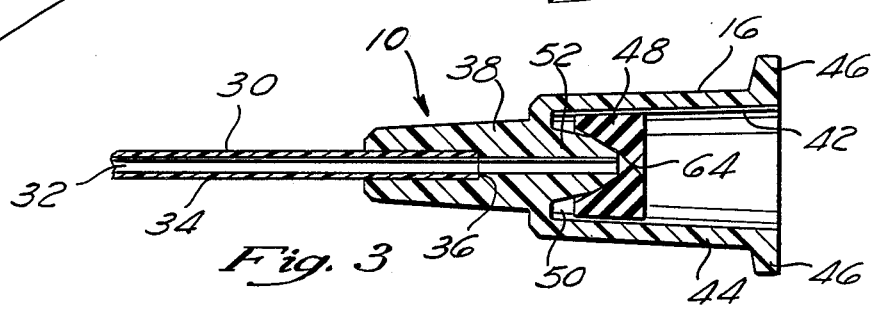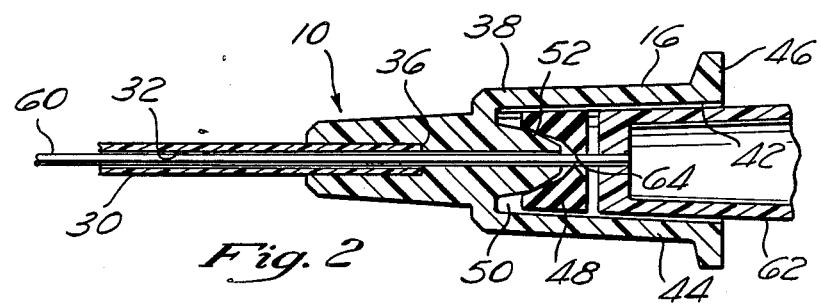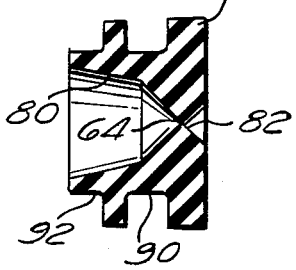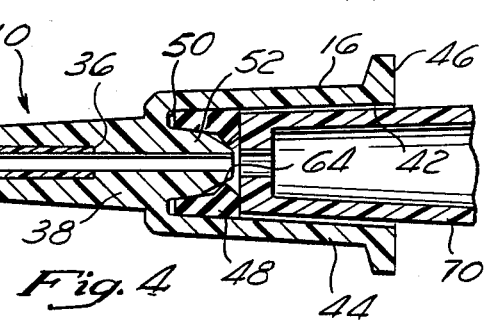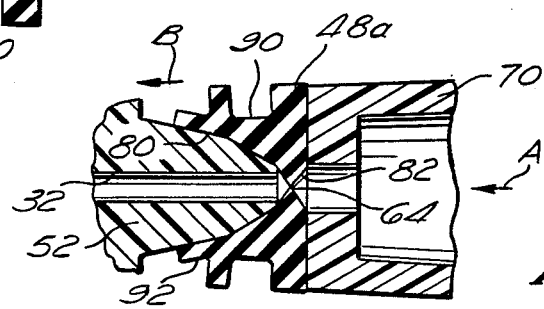

SELF-OCCLUDING INTRAVASCULAR CANNULA ASSEMBLY

BACKGROUND OF THE INVENTION

This application pertains generally to the medical arts and more particularly to an improved self-occluding cannula assembly for insertion into blood vessels or various body cavities.

The invention is particularly applicable to flexible intravascular cannulae of the type commonly used to administer intravenous infusions and/or to monitor pressures within arteries and/or veins of the human body. Accordingly, the invention will be described with particular refererence to such applications. It must be appreciated, however, that the invention has utility in numerous other applications wherein it is desirable to prevent or limit back flow of bodily fluids from a tubular cannula. Examples of other types of cannulae wherein the present invention may be utilized include, but are certainly not limited to; trocars for intra-abdominal or intra-thoracic insertion; long flexible catheters used for monitoring central venous pressures and for centrally administering drugs and various infusates; and various indwelling semi-permanent catheters such as the type commonly used in the administration of total parenteral alimentation.

Although many of the cannulae in which the invention will be used may incorporate removable introducer needles or stylets to effectuate puncture of soft tissues, it must be further appreciated that the utility of the invention is not limited to such needle-bearing devices. In fact, the occluding means of the present invention may be employed with even the simplest types of medical tubing to prevent back flow of fluids therefrom.

It is common practice in the medical field to insert tubular cannulae into blood vessels for the infusion of various fluids and/or the monitoring of intravascular pressures. One simple intravenous cannula assembly of the prior art comprises a flexible cannula sheath having a rigid introducer needle positioned axially therewithin. The bevelled tip of the hollow introducer needle extends a short distance beyond the distal tip of the cannula to permit easy penetration of the skin and underlying tissues. When the needle tip enters the target blood vessel, blood immediately fills the lumen of the needle and advances proximally to a transparent receptical on the needle hub where it may be readily viewed. Alternatively the needle hub may be connected to a syringe wherein a small amount of the blood may be visably withdrawn into an existing quantity of saline solution. Thereafter, the introducer needle is withdrawn. Thus, the cannula sheath remains in place as a means for subsequent infusion of intravenous fluids and/or monitoring of intravascular pressures.

Because the flexible cannula sheath comprises a generally hollow tube, blood will rapidly back flow (i.e. flash back) through the inner lumen of the cannula upon withdrawal of the introducer needle. As a result, a certain amount of blood invariably flows out of the proximal end of the cannula immediately after withdrawal of the introducer needle. Regardless of how adept the user may be at attaching an appropriate solution administration line or other auxiliary tube to the proximal end of the cannula, a certain amount of blood loss is likely to occur.

Likewise, if the attendant solution administration line or other tube subsequently becomes disconnected from the cannula, blood will immediately back flow from the cannula and may continue to flow therefrom until the disconnected line is discovered and reconnected.

Indeed, any unnecessary back flow of blood from the cannula lumen is undesirable from a standpoint of general hygiene as well as in view of the present potential for blood born disease transmission. Serious diseases such as Hepatitis and Acquired Immune Difficiency Syndrome are known to be transmissible to health care workers and others who come in contact with infectous blood.

Thus given the desirability of preventing the unnecessary back flow and leakage of blood from the cannula, a number of arrangements have been devised whereby the user of the cannula may pinch off or otherwise obstruct the cannula lumen. Examples of such prior art devices are found in U.S. Pat. Nos. 3,875,935 (Mellor), 2,682,874 (Hickey), 4,192,304 (Millett), 3,856,020 (Kovac), and 3,856,010 (Moorehead). These prior United States Patents disclose various means for valving, blocking, clamping, pinching, or otherwise restricting certain types of medical tubing for purposes of preventing fluid back flow thererfrom.

Specifically, U.S. Pat. No. 4,192,304 (Millett) describes an intravascular catheter assembly comprising a pliable cannula sheath, having an introducer needle disposed axially therewithin. A pair of laterally extending external wings are formed on the the proximal end of the cannula. One of the wings bears a pinching protuberance. Upon withdrawal of the introducer needle, the user of the cannula may manually fold one of the wings over the cannula body so as to cause the pinching protuberance to exert occluding pressure on the cannula. Thus, so long as pressure is applied to the folded wing, the pinching protuberance will effectively occlude the cannula lumen. Such occlusion is purported to prevent undesirable back flow of fluids from the cannula.

Another exemplary prior art device is described in U.S. Pat. No. 3,856,010 (Moorehead). The device described therein comprises a flexible cannula sheath having an introducer needle disposed axially therewithin. The Moorehead further incorporates a resilient means which is manually compressable to control the flow of fluid through the cannula. As the introducer needle is withdrawn, the user must positively and affirmatively apply pressure to a projection, which upon passage of the needle, results in closure of a valve member so as to prevent the flow of fluid through the cannula lumen. Upon release of such pressure, the valve member relaxes, and the cannula lumin resumes its normal shape permitting free fluid flow therethrough.

Yet another exemplary prior art device is disclosed in U.S. Pat. No. 3,875,938 (Mellor). The Mellor device includes a bifurcated cannula assembly wherein a needle-like "puncture rod" is disposed axially within a flexible cannula sheath. The Mellor device includes a means whereby the user may pinch off the cannula lumen between the time that the "puncture rod" is removed and the subsequent coupling of auxilliary infusion tubing to the proximal end of the cannula.

At least one other intravenous cannulation device of the prior art employs a bifurcated design wherein a separate side arm or secondary infusion port is provided in addition to a proximal extension of the lumen through which the introducer needle is withdrawn. The introducer needle may thus be withdrawn through a latex membrane, flap-like seal, or other sealing closure located separate and apart from the side arm infusion port. Thereafter, the infusion of fluid, withdrawal of blood or monitoring of pressures is carried out through the side arm port while the sealed channel through which the needle was withdrawn remains usable only as a self sealing injection port for the periodic injection of medications, or piggyback administration of a second intravenous fluid.

While each of the prior art devices may indeed be capable of stopping or at least limiting, the back flow of blood from certain types of tubes in certain situations, it must be appreciated that none of the prior art devices provides an occlusion means that is fully self activating (i.e. user passive) so as to automatically halt the flow of fluid through the cannula upon withdrawal of the introducer needle and subsequently capable of re-occluding the cannula upon inadvertent disconnection of any attendant infusion/monitoring line. Indeed, many of the prior art occlusion devices require rather intricate manual manipulation and constant manual attendance in order to effect occlusion of the cannula lumen. Additionally, prior art devices which incorporate elaborate secondary infusion ports, side arms, and other bifurcated arrangements may be expensive to manufacture and confounded with unnecessary complexity in clinical use.

Accordingly, there currently exists a need in the art for a fully self-actuating occlusion means which will serve to passively, automatically occlude the cannula lumen upon withdrawal of an existing introducer needle as well as to subsequently re-occlude the cannula lumen upon inadvertent disconnection of any infusion and/or monitoring line from the proximal end of the cannula. The present invention overcomes these shortcomings of the prior art in addition to providing other advantages over the existing devices.

BRIEF DESCRIPTION OF THE INVENTION

In accordance with the present invention, there is provided a self-occluding intravascular cannula assembly which comprises a pliable cannula sheath having an introducer needle retractably axially disposed therewithin such that the bevelled distal tip of the needle extends slightly beyond the distal tip of the cannula sheath. A connecting hub is formed on the proximal end of the cannula to fluidly connect the cannula to a separate infusion tube or monitoring line. At least one occluding member is positioned within the cannula assembly. Such occluding member is alternately disposable in an "occluded" configuration and a "non-occluded" configuration. In its "occluded" configuration, the occluding member will effect blockage of the inner cannula lumen so as to prevent at least proximally directed flow of fluids from the cannula. In its "non-occluded" configuration, the occluding member will permit free fluid flow through the cannula lumen thereby permitting the desired infusion of fluid and/or the transmission of pressure pulses through the fluid filled cannula. Thus, after the needle/cannula assembly has been inserted to its desired location within a blood vessel, the introducer needle is withdrawn. Thereafter, the occluding member will immediately and automatically assume its "occluded" configuration to prevent backflow of blood from the cannula. Subsequently, when the infusion tubing or other auxillary tube is connected to the proximal end of the cannula assembly, the physical act of connecting such tube will induce the occluding member to move to its "non-occluded" configuration. Such "non-occluded" configuration will permit distal flow of infusate and/or proximal transmission of pressure pulses through the cannula. Thereafter, if the infusion tubing is purposefully or inadvertently disconnected from the cannula, the occluding member will again automatically assume its "occluded" configuration so as to prevent the back flow and leakage of blood from the cannula until such time as the disconnected tubing has been properly reconnected.

In accordance with another aspect of the invention, the occluding member may be in the form of an elastic obturator member positioned within the cannula hub and alternately disposable in "occluded" and "non-occluded" configurations. Preferably, the obturator member will be generally in the form of a cylindrical disc, having a resiliently openable and closable central aperture extending therethrough. The disc shaped obturator is positioned transversly within the cannula lumen with the introducer needle initially disposed through the tiny central aperture of the obturator such that the resilient body of the obturator member will circumferentially abut the outer surface of the introducer needle. After the tip of the cannula assembly has been inserted into the desired vessel, the introducer needle is withdrawn proximally through the obturator member. Immediately upon withdrawl of the needle, the aperture of the obturator member snaps fully closed so as to effect rapid and complete occlusion of the cannula lumen. Thereafter, the insertion of a male tubing connector into the cannula hub will exert pressure on the obturator member thereby shifting the position of the obturator and causing the central aperture to become dilated. Such dilation of the central aperture will permit fluid to flow through the cannula lumen as desired. If, however the attached infusion tubing should subsequently become disconnected from the cannula, the elastic obturator member will resiliently spring back to its occluded configuration wherein it will prevent back flow and leakage of blood from the cannula. The obturator member will then remain in such occluded configuration until the infusion tubing has been reconnected to the cannula.

In accordance with a further aspect of the invention, the cannula hub may be in the form of a standard female Leur connector capable of receiving a standard male connector and adapted such that the physical act of inserting the male connector into the female connector will cause the occlusion means of the cannula assembly to shift from its "occluded" position to its "non-occluded" position.

In accordance with even further aspect of the invention, the central aperture of the obturator member may be formed as a pinhole, slit, cross slits or any other openable and closable configuration capable of achieving the desired function.

In accordance with an even further aspect of the invention, the cannula hub may include one or more internally formed dilator projection(s). Such dilator projection is positioned distal to the obturator member and configured to aid in dilating the central aperture of the obturator member as the obturator member is depressed distally into a preformed seating groove. Such dilator projection may be nothing more than a raised nub which is operative to exert pressure on the elastic material of the obturator, thereby spreading or stretching the central aperture causing the previously occluded cannula lumen to become unoccluded and free flowing.

A principal object of the invention is to provide a user passive, self-occluding intravascular cannula which will prevent the back flow of bodily fluids from the proximal end of the cannula following insertion of the cannula within a desired vessel and until such time as a second tube is firmly connected thereto.

Another object of the invention is to provide a self-occluding intravascular cannula which will automatically assume an "occluded" configuration in the event that the second tube is inadvertently or purposely disconnected therefrom. Such automatic occlusion of the cannula lumen will prevent the inadvertent back flow of blood from the proximal end of the cannula until such time as the infusion and/or monitoring line is reconnected thereto.

Yet another object of the invention is to prevent or minimize the transmission of blood born diseases such as hepatitis and Acquired Immune Difficiency Syndrome to health care workers and others by preventing the unnecessary backflow of blood from an intravascular cannula.

A still further object of the invention is to provide a self-occluding intravascular cannula wherein the occluding means of the cannula circumferentially abutts the outer surface of the introducer needle so as to thoroughly wipe any adherent blood from the needle as it is withdrawn from the cannula.

These and other objects and advantages of the present invention will become apparent to those skilled in the art upon reading the following detailed description and consideration of the accompanying drawings.

BRIEF DESCRIPTION OF THE DRAWINGS

In the drawings:

FIG. 1 is a perspective view of a preferred intravascular cannula assembly of the present invention operatively disposed within a blood vessel and having a separate infusion line fluidly connected thereto;

FIG. 2 is an exploded cross-sectional view of selected internal components of a preferred intravascular cannula assembly of the present invention;

FIG. 3 is a longitudinal sectional view of a preferred intravascular cannula assembly of the present invention wherein the occluding means is disposed in its "occluded" configuration;

FIG. 4 is a longitudinal sectional view of a preferred intravascular cannula assembly of the present invention having an introducer needle axially disposed within the inner lumen of the cannula;

FIG. 5 is a longitudinal sectional view of a preferred intravascular cannula of the present invention wherein the occluding means is in its "non-occluded" configuration and an attendant infusion line is connected to the cannula assembly;

FIG. 6 is a modified obturator type occluding member having annular grooves formed in the outer periphery thereof to facilitate transition of the obturator between the "non-occluded" and "occluded" positions;

FIG. 7 is a longitudinal sectional view of the modified obturator disc of FIG. 6 positioned over a dilator member within the catheter assembly as the male Leur connector of a fluid infusion line is being advanced against the obturator member.

DESCRIPTION OF A PREFERRED EMBODIMENT

Referring to FIG. 1, there is shown a self occluding intravascular cannula assembly 10 of the present invention inserted into a vein of the human subject. An infusion tube 12 is connected to the cannula assembly 10 by way of a conventional male luer connector 20 so as to provide for continuous administration of the desired infusate.

The intravascular cannula assembly 10 comprises a flexible tube-like sheath shown in dotted lines, which has been inserted percutaineously into the desired vein. A proximal hub 16 forms a portion of the cannula assembly 10. As shown, the hub 16 of the cannula assembly 10 comprises a mating female Leur connector, having a Leur lock flange 18 extending peripherally therearound.

One important feature of the present invention is the ability of the cannula assembly 10 to "self-occlude." Such self-occlusion prevents the undesirable back flow and leakage of blood from the cannula following retraction of the introducer needle, and also prevents such back flow and leakage of blood in the event that the attendant infusion line 12 is inadvertently or accidentally detached from the cannula assembly 10.

A preferred means by which such self-occluding feature may be formed within the cannula assembly 10 may be fully appreciated from the longitudinal sectional views shown in FIGS. 2 through 4. FIGS. 2 through 4 commonly show a portion of the flexible tubular cannula 30 having an inner lumen 32 and an outer tubular wall 34. The outer wall 34 of the cannula 30 is formed of a flexible, physiologically inert material such as polytetrafluoroethylene. The proximal tip 36 of the flexible cannula sheath 34 is firmly fused within the body of the proximal hub 38. The body of the hub is formed of a medical grade molded plastic material which is generally more rigid than the flexible material which forms the cannula sheath 34. The inner lumen 32 of the cannula assembly 10 extends beyond the proximal end 36 of the flexible sheath 34 and continues proximally through a portion of the body of the cannula hub 38 and into the open bore 42 of the hub 38.

A female Leur connector 44 is formed on the proximal end of the hub 38. The inner bore 42 of the female connector 44 portion of the hub 38 is configured to accomodate a corresponding male Leur connector of the type commonly affixed to intravenous solution administration tubes or other types of infusion/monitoring lines. A Leur-lock flange 46 extends periferally around the proximal end of the female Leur connector 44 so as to accomodate an appropriately threaded locking fixture which may optionally be formed on the corresponding male connector.

The self-occluding feature of the present invention is owed, in this preferred embodiment, to the presence of a specifically formed and positioned occluding means or valving member. In this preferred embodiment, the occluding means comprises an elastomeric or resilient obturator member 48 which is disposed within the cannula hub 38. The obturator member 48 is generally seated within a positioning groove 50 which extends around a conical dilator projection 52. The inner lumen 32 of the cannula assembly 10 extends fully through the dilator projection 52 as shown. A major conical shaped aperture 80 is formed on the distal side of the obturator member 48 so as to permit the member 48 to seat generally over the conical dilator projection 52. As will be further described herein, it is the interaction of the dilator projection 52 with the elastic obturator member 48 which, in part causes the cannula assembly of the present invention to shift from its "occluded" configuration to its "non-occluded" configuration.

Referring specifically to FIG. 2, it will be appreciated that, prior to insertion of the cannula into the desired vessel, an introducer needle 60 is axially disposed within the cannula lumen 32 such that the bevelled tip of the needle 60 protrudes slightly beyond the distal end of the flexible cannula sheath 34. The proximal hub 62 of the needle 60 is sized and configured to fit slidably within the inner bore 42 of the female Leur connector 44 thereby holding the needle 60 and cannula assembly 10 in firm union during insertion into a desired vein. After the cannula assembly 10 (with the introducer needle 60 positioned therein) has been inserted into the desired blood vessel, the needle 60 is withdrawn, leaving the flexible cannula sheath 30 in place within the blood vessel. As the needle 60 is withdrawn, the obturator 48 will wipe any adherent blood from the outer surface of the needle 60. Immediately upon withdrawal of the needle 60, the central aperture 64 of the obturator member 48 will close due to its internal resiliency, thereby preventing back flow of blood from the cannula. The obturator member 48 will remain in such occluded position until such time as the male connector 16 of an attendant infusion line has been fully inserted within the bore 42 of the cannula hub 38. Such insertion of a male connector 16 into the cannula hub 38 will exert distally directed pressure causing the obturator 48 to move distally within the seating groove so causing resultant dilation of the aperture 60 as will be further described herein.

The "occluded" configuration assumed by the obturator 48 upon withdrawal of the needle 60 is shown specifically in FIG. 3. With the needle 60 having been fully withdrawn from the cannula lumen 32, the pinhole aperture 64 of the resilient obturator 48 assumes a fully closed configuration so as to occlude the proximal end of the cannula lumen 32 and to prevent the back flow of blood therefrom.

Complete and rapid closure of the aperture 64 is facilitated by the specific positioning of the obturator 48. As shown in FIG. 3, the base of the obturator 48 is disposed within an annular seating groove 50. In its unoccluded position the obturator 48 is not fully advanced into the seating groove 50 thereby leaving an unoccupied area or void at the base of the annular seating groove 50. The conical dilator projection 52, which is positioned in the center of the annular seating groove 50, is sized and configured to fit within a corresponding conical notch 80 on the distal side of the obturator 48. So long as the obturator 48 remains in its relaxed position the dilator projection 52 does not exert sufficient proximally directed pressure on the obturator 48 to cause dilation of the aperture 64. It is only when the obturator 48 is depressed distally into its annular seating groove 50 that the conical dilator projection 52 will interact with the obturator 48 to cause dilation and opening of the aperture 64. Such depression of the obturator 48 into the annular groove 50 may be caused by the firm insertion of a male Leur connector 62 into the female bore 42. The manner by which insertion of a male Leur adaptor will cause the obturator to assure its "non-occluded" configuration is shown in FIG. 4.

Referring to FIG. 4, the tip of the male connector 70 is inserted within the female bore 42 of the female Leur portion 44 of the cannula hub 38. A normal amount of hand pressure is applied distally as the male connector 70 is inserted into the cannula hub. The resilient obturator 48 is thus forced distally into the previously unoccupied region of its annular seating groove 50. Such distal movement of the resilient obturator 48 causes the conical dilator member 52 to press against and to dilate aperture 64 in the manner shown. Such dilation of the aperture 64 effectively opens the cannula lumen 32 thereby permitting the free flow of infusion fluid through the cannula. It should also be appreciated that while the obturator 48 remains in such "non-occluded" configuration, the cannula lumen will remain sufficiently unobstructed to permit periodic withdrawal of blood or continuous monitoring of pressures through the use of an appropriately connected pressure transducer.

The conical dilator projection 52 and the resilient obturator member 48 are shown in greater detail in the exploded view of FIG. 5. As shown in FIG. 5, the obturator member 48 comprises a resilient and elastic cylindrical disc made of latex rubber or some other elastomeric material having the requisite elasticity, memory and other physical properties to accomplish the desired objective. The obturator member 48 is a generally cylindrical body having a large conical notch 80 formed within one end of the cylinder and a small conical notch 82 within the opposing end thereof. The apical portions of the two opposing conical notches 80, 82 converge within the center of the disc 48 to form a tiny pinhole aperture 62 extending therebetween So long as the elastomeric material of the obturator member 48 remains fully relaxed and unstretched the small aperture 62 will be closed sufficiently to prevent the flow of fluid therethrough within the range of intravascular pressures encountered. When, however the elastic material of the obturator 48 is stretched outwardly toward the periphery of the disc, the aperture 62 will become dilated or opened up. Such opening of the aperture 62 effectively relieves the occlusion of the cannula lumen 32 and permits fluid flow therethrough.

The large conical notch 80 of the resilient obturator 48 and the annular seating groove 50 may be specifically configured such that the obturator 48 will remain resiliently biased toward its "non-occluded" position. Thus, whenever an existing source of distally directed pressure, such as a properly inserted male connector 70, is removed from its position within the female Leur portion 44 of the cannula hub 38, the resilient obturator 48 will immediately and automatically spring back into its original "occluded" configuration as represented in FIG. 3. Such will give rise to rapid self-occlusion of the cannula in the event that the infusion tubing or monitoring line is inavertently disconnected due to movement of the patient or snagging of the infusion line.

In order to achieve its desired function, the obturator member 48 will be made of a material which is resilient, stretchable, and possessed of sufficient memory to function in the desired manner. In order to accomodate the use of a somewhat dense or slightly uncompressible materials, it may be desirable to form a plurality of peripheral notches or grooves around the rim of the disc-like obturator 48. Such notches or grooves will facilitate compaction of the obturator 48 within its seating groove 50 as it shifts from its "non-occluded" to "occluded" configuration. An example of such notch and groove structure is shown in FIGS. 6 and 7.

FIG. 6 shows the modified obturator member 48a which, like its unmodified counterparts, has a large conical notch 80 and small conical notch 82 converging centrally to form tiny pinhole aperture 62. In the view of FIG. 6, the modified obturator member 48a is in its fully relaxed "occluded" configuration. The aperture 62 is thus closed. A circumferential groove 90 extends around the mid-region of the periphery of the disc shaped obturator member 48 while a similar right angular cutaway region 92 extends around the distal most portion thereof. The provision of the circumferencial groove 90 and the cutaway region 92 serves to reduce the physical mass of the obturator member 48 without interfering with its function. Such grooved construction allows the obturator 48a to be easily compressed into the conical seating groove 50 and also serves to improve the resiliency and proximal bias which causes the obturator 48a to spring back to its non-occluded position immediately upon removal of the male connector from the cannula hub 38.

FIG. 7 shows the modified obturator member 48a in its "occluded" configuration wherein the aperture 62 of the modified obturator 48a is fully relaxed in its "occluded" configuration resulting in full closure of the lumen 32. However, as shown, the distal tip of a corresponding male connector 70 is being advanced in the direction of arrow A and is about to come in contact with the modified obturator member 48a. Upon making such contact, and exerting distally directed pressure on the modified obturator member 48a, the member 48a will be slidably depressed over the conical dilator projection 52 as indicated by arrow B. Such will result in a dilation of the aperture 52 relieving the previous occlusion of the cannula lumen 32.

It should be appreciated from these drawings that the self-occluding cannula assembly of the present invention has many advantages. For example, because the aperture 64 of the obturator member 48, 48(a) fits snuggly around the introducer needle 60 while it is withdrawn from the cannula lumen 32, such will have the desirable effect of wiping blood from the outer walls of the needle as it is being withdrawn from its position within the cannula lumen. Such blood wiping effect will further limit the potential for transmission of blood born infections.

Also, because the obturator member 48, 48a serves to immediately seal off the cannula lumen upon withdrawal of the introducer needle or detachment of any attendant infusion/monitoring line, the inner bore of the cannula hub will tend to remain clean and free of blood. Such is desirable in that leakage of blood into the bore 42 of the connector 44 could lead to the formation of clots and incrustations around the walls of the bore 42. The presence of such clots or incrustations within the bore 42 may serve to harbor bacteria and, if carried into the cannula lumen, could result in the inadvertent introduction of small emboli.

Additionally, it must be appreciated that the invention has been described herein with reference to a presently preferred embodiment. Indeed, numerous modifications and alternations may be made to such preferred embodiment without departing from the spirit and scope of the invention. For example, in the preferred embodiment, the occluding means which serves to occlude the cannula lumen is specifically described as a resilient obturator member 48, 48a. In alternative embodiments, other types of diaphragms, plugs, valves, flaps, and the like may be utilized in place of the obturator member which has been described with respect to this preferred embodiment. Also, the preferred embodiment is specifically described as an "intravenous cannula" having an introducer needle disposed therein. However, the invention may be incorporated into many other types of tubes, catheters, trocars and the like. Accordingly, it is intended that all such modification and alterations be included within the scope of the appended claims and the equivalents thereof.

Having thusly described the invention, what is claimed is:

1. A self-occluding cannula assembly comprising:
   a generally tubular cannula sheath having a proximal end, a distal end, and an inner lumen extending axially therethrough;
   a connecting hub formed on the proximal end of said cannula sheath, said connecting hub having an axial bore formed therein, said axial bore being fluidly consistent with the inner lumen of said cannula sheath; and
   an occluding means comprising:
   a frusto conical dilator projection;
   an annular seating groove formed around said frusto conical dilator projection; and
   an obturator member comprising a generally disc shaped body disposed transversely within said connecting hub, proximal to said dilator projection, said disc shaped body having at least one elastically openable and closable aperture and at least one notch formed therein;
   said obturator member normally residing in an "occluding" position wherein said openable and closable aperture remains closed so as to substantially preclude fluid from flowing through said cannula lumen;
   said obturator member being slidably movable relative to said dilator projection such that the application of distally directed pressure against said obturator member will cause said obturator member to distally advance to a "non-occluding" position wherein at least a portion of said obturator member is advanced into said seating groove and the notch portion of said obturator member is advanced over at least a portion of said frusto conical dilator projection such that said dilator projection exerts sufficient pressure against said obturator member to cause said openable and closable aperture to assume an open configuration whereby fluid is permitted to flow through said cannula lumen and further whereby, upon removal of said distally directed pressure, said obturator member will resiliently return to its "occluding" position.

2. The self-occluding cannula assembly of claim 1 further comprising:
   an introducer needle slidably axially disposed within said cannula lumen,
   said introducer needle comprising an elongate needle shaft having a sharpened distal tip;
   said sharpened distal tip extending beyond the distal end of said flexible cannula sheath so as to facilitate percutaneous insertion of said cannula sheath.

3. The self-occluding cannula assembly of claim 2 wherein said introducer needle extends through the openable and closable aperture of said obturator member.

4. The self-occluding cannula assembly of claim 3 wherein the openable and closable aperture of the obturator member, when in its "occluding" position fits snugly about said introducer needle so as to wipe adherent fluid from the introducer needle as said introducer needle is proximally withdrawn from the cannula assembly.

5. The self-occluding cannula assembly of claim 4 wherein said introducer needle comprises a generally hollow needle having an open axially extending inner lumen through which fluid may flow upon insertion of the distal tip of the needle into a fluid filled anatomical structure.

6. The self-occluding cannula assembly of claim 1 wherein at least a portion of said cannula hub comprises a female tubing connector having an inner bore into which a correspondingly shaped male tubing connector may be inserted.

7. The self-occluding cannula assembly of claim 6 wherein said cannula hub and said obturator member are configured and positioned such that insertion of said male tubing connector into said female tubing connector will exert sufficient distally directed pressure against said obturator member to cause said obturator member to move from its "non-occluding" position to its "occluding" position.

8. The self-occluding cannula assembly of claim 1 wherein said obturator member is provided with at least one circumferential groove extending therearound to facilitate compression of at least a portion of said obturator member into said annular seating groove and to improve the resiliency by which said obturator member returns to its "occluding" position from its "non-occluding" position.

* * * * *